United States Patent [19]

Klemann et al.

[11] Patent Number: 4,877,871

[45] Date of Patent: Oct. 31, 1989

[54] SYNTHESIS OF SUCROSE POLYESTER

[75] Inventors: Lawrence P. Klemann, Somerville; John W. Finley, Whippany; Anthony Scimone, Cedar Grove, all of N.J.

[73] Assignee: Nabisco Brands, Inc., East Hanover, N.J.

[21] Appl. No.: 206,656

[22] Filed: Jun. 14, 1988

[51] Int. Cl.[4] .................. C07G 17/00; C07H 13/02; C09F 5/08

[52] U.S. Cl. .................. 536/124; 536/119; 260/410

[58] Field of Search ............... 536/119, 124; 260/410

[56] References Cited

U.S. PATENT DOCUMENTS

| | | | |
|---|---|---|---|
| 2,853,485 | 9/1958 | Werner et al. | 536/119 |
| 2,893,990 | 7/1959 | Hass et al. | 536/119 |
| 2,931,802 | 4/1960 | Toney | 536/119 |
| 2,938,898 | 5/1960 | Werner et al. | 536/119 |
| 2,948,717 | 8/1960 | Babayan et al. | 536/119 |
| 3,057,743 | 10/1962 | Toney et al. | 536/119 |
| 3,096,324 | 7/1963 | Goins et al. | 536/119 |
| 3,248,381 | 4/1966 | Nobile et al. | 536/119 |
| 3,251,827 | 5/1966 | Schnell et al. | 536/119 |
| 3,378,542 | 4/1968 | O'Boyle | 536/119 |
| 3,480,616 | 11/1969 | Osipow et al. | 536/114 |
| 3,600,186 | 8/1971 | Mattson et al. | 536/119 |
| 3,714,144 | 1/1973 | Feuge et al. | 536/119 |
| 3,792,041 | 2/1974 | Yamagishi et al. | 536/119 |
| 3,963,699 | 6/1976 | Rizzi et al. | 536/119 |
| 3,985,750 | 10/1976 | Protiva et al. | 544/375 |
| 4,005,195 | 1/1977 | Jandacek | 536/119 |
| 4,126,628 | 11/1978 | Pacquet | 260/404.5 |
| 4,142,041 | 2/1979 | Kanai et al. | 536/23 |
| 4,211,865 | 7/1980 | Ferruti et al. | 536/48 |
| 4,241,054 | 12/1980 | Volpenhein et al. | 536/119 |
| 4,264,583 | 4/1981 | Jandacek | 536/119 |
| 4,340,728 | 7/1982 | Endo et al. | 536/23 |
| 4,377,686 | 3/1983 | Feuge et al. | 536/119 |
| 4,446,165 | 5/1984 | Roberts et al. | 426/602 |
| 4,461,782 | 7/1984 | Robbins et al. | 426/549 |
| 4,517,360 | 5/1985 | Volpenhein | 536/119 |
| 4,518,772 | 5/1985 | Volpenhein | 536/119 |
| 4,543,353 | 9/1985 | Faustini et al. | 514/239.2 |
| 4,611,055 | 9/1986 | Yamamoto et al. | 536/119 |

OTHER PUBLICATIONS

Fieser, L. E. and Fieser, M., *Reagents for Organic Synthesis*, 1967, pp. 231–235.
Fieser, M. and Smith, J. G., *Reagents for Organic Synthesis*, vol. 13, 1988, pp. 107–108.
Raphael, R. A., et al., eds., *Advances in Organic Chemistry*, vol. 3, 1963, pp. 115–121.
Reichen, W., 78 *Chem. Rev.* 569–588 (1978).
Hamm, D. J., 49 *J. Food Sci.* 419–428 (1984).
Markley, K. S., ed., *Fatty Acids*, Interscience Pub. Co., N.Y., 1961, vol. 2, pp. 848–850.
Mattson, F. H. and Nolen, G. A., 102 *J. Nutrition* 1171–1175 (1972).
Osipow, F. D., et al., 48 *Ind. Eng. Chem.* 1459–1462 (1956).

*Primary Examiner*—Ronald W. Griffin
*Assistant Examiner*—Everett White
*Attorney, Agent, or Firm*—Richard Kornutik

[57] ABSTRACT

Sucrose fatty acid polyesters having six to eight hydroxyl groups esterified per molecule are synthesized in a dicyclohexylcarbodiimide coupling of sucrose lower esters with fatty acids in tetrahydrofuran in the presence of 4-dimethylaminopyridine. The procedure avoids the solubility, viscosity and phase separation problems encountered in previously described syntheses, and the product of the condensation is free of contamination by alkali metal soaps used and the sucrose decomposition products formed in other methods.

31 Claims, No Drawings

SYNTHESIS OF SUCROSE POLYESTER

BACKGROUND OF THE INVENTION

This invention relates to a synthesis of sucrose fatty acid polyesters.

Fatty acid esters of sucrose were first prepared commercially for use in the food industry as nonionic surfactants, and the mono-, di- and tri- esters were found to be useful as emulsifiers (Osipow, L., et al., 48 Ind. Eng. Chem. 1459 (1956)). Whereas these lower esters of sucrose readily hydrolyze to form normal food components on digestion in mammals, it was discovered that sucrose and structurally-related polyols which had more than four esterified hydroxyl groups were less readily absorbed (Mattson, F. H., and Nolen, G. A., 102 J. Nutrition 1171 (1972)).

Sucrose polyesters which have at least four hydroxyl groups esterified with fatty acid residues per sucrose molecule have many of the physical properties of ordinary triglyceride fat. Since sucrose polyesters are comparatively less digested or absorbed and thus are relatively low in available calories, they are useful as low calorie replacements of edible fats and oils in food products (Hamm, D. J., 49 J. Food Sci. 419 (1984)). Consequently, in recent years the scientific and industrial community has focused attention on this class of compounds. Sucrose polyesters have been suggested for a variety of low calorie food compositions (e.g., U.S. Pat. Nos. 3,600,186, 4,446,165, and 4,461,782).

Further research on the dietary use of sucrose polyesters led to the finding that certain non-absorbable, non-digestible polyesters interfere with the body's absorption of cholesterol and thereby provide a potential means for treating hypercholesterolemia (U.S. Pat. No. 4,005,195). Pharmaceutical studies of sucrose polyesters were expanded. Sucrose polyesters have since been suggested for treating acute and chronic exposures to lipophilic toxins (U.S. Pat. No. 4,241,054), and for dissolving gallstones (U.S. Pat. No. 4,264,583).

A variety of methods have been developed to synthesize this class of dietary and pharmaceutical compounds. These methods followed classical esterification procedures similar to those outlined for fatty acid esters generally; sucrose octapalmitate and octastearate were prepared as early as 1921 (Markley, K. S., ed., *Fatty Acids*, Interscience Pub. Co., N.Y., 1961, vol 2, p. 849). The methods include the reaction of sucrose with acid anhydrides (U.S. Pat. Nos. 2,931,802, 3,057,743 and 3,096,324) or with acid halides (U.S. Pat. Nos. 2,853,485, 2,938,898, and 2,948,717), and the transesterification of fatty acid esters with sucrose in a solvent (U.S. Pat. Nos. 2,893,990 and 3,248,381). The reactions were plagued by solubility problems, since the properties of the sucrose are entirely different from fats or fatty acids (Osipow, L., et al. supra at 1459). The solvents employed, notably dimethylformamide, which was found to be particularly suitable, were expensive and toxic. The protocols devised to remove solvent after the reaction were possible in practice only with great difficulty (U.S. Pat. Nos. 3,378,542 and 4,611,055).

The so-called "transparent" or "micro-emulsion" process was suggested to overcome these drawbacks of the solvent system. In this method, a fatty acid ester is dispersed in a solution of a solvent such as propylene glycol or water with the aid of an emulsifier such as an alkali metal fatty acid soap to form a micro-emulsion, and the solvent is removed from the emulsion. The reaction is then carried out in the absence of solvent as if the reactants were miscible or if they were dissolved in a mutual solvent, and the reaction product does not contain any solvent (U.S. Pat. No. 3,480,616). However, removing the emulsification solvent while maintaining the micro-emulsion is difficult and the sucrose polyesters formed are contaminated with the soaps used as emulsifiers (U.S. Pat. No. 4,611,055).

A solvent-free synthetic technique was reported to overcome the problems of both the solvent and the micro-emulsion methods (U.S. Pat. No. 3,963,699). This synthesis is a transesterification between sucrose and fatty acid lower alkyl esters, which are simply heated together in an inert atmosphere. Since sucrose melts at about 185° C. and starts to decompose after a few minutes at its melting point, the rate of sucrose degradation on heating must be retarded; for this an alkali-free soap is added (U.S. Pat No. 3,714,144). Subsequent patents disclose improvements in yield by suggesting catalysts and changes in reactant ratios (U.S. Pat. Nos. 4,517,360 and 4,518,772).

The solvent-free transesterification system has drawbacks, however. The unreacted alkali metal soaps used to keep the sugar from decomposing must be separated from the sucrose polyester product afterwards (U.S. Pat. No. 4,611,055). The product is further contaminated by sucrose decomposition products because sucrose is so thermally unstable that it is difficult to melt without some thermal cracking. Thus, sucrose polyesters made using this method are often described as colored. (See, for instance, Example I of U.S. Pat. No. 3,963,699, and Example 6 of U.S. Pat. No. 4,611,055, which yield, respectively, "light yellow" and "pale yellow" sucrose polyesters, and the examples in U. S. Pat. Nos. 4,517,360 and 4,518,772 disclose bleaching steps.)

To obtain a homogeneous melt, it is necessary to stir the system, and the reactants are viscous and tend to agglomerate (U.S. Pat. No. 3,251,827). The reactants have poor affinity for one another, and the sucrose fatty acid ester intermediates that form hydrolyze or saponify readily (U.S. Pat. No. 3,792,041). Furthermore, to obtain a high degree of transesterification, the molar ratio of fatty acid esters to sucrose must be in excess of a stoichiometric amount, and a reaction mixture containing such an excess of the fatty acid esters, which are less viscous than sucrose, is easily susceptible to phase separation, which adversely affects the reaction (U.S. Pat. No. 4,611,055).

SUMMARY OF THE INVENTION

An objective of the present invention is to provide a process for producing sucrose fatty acid polyesters which is free from the above-described disadvantages. Problems resulting from the thermal instability of sucrose and from product contamination by alkali metal fatty acid soaps are obviated by eliminating the use of sucrose and soaps in the synthetic procedure. Solubility, viscosity, and phase separation difficulties are avoided by the use of reactants soluble in a solvent medium, which can be removed after the reaction takes place.

It has now been found that sucrose fatty acid polyesters may be synthesized by condensing lower sucrose fatty acid esters with fatty acids in a solvent in the presence of a catalyst and an effective amount of a condensation agent. Preferably, the reaction is carried out between a sucrose diester and a fatty acid in an aprotic solvent in the presence of a tertiary amine and an effective amount of dicyclohexylcarbodiimide.

DETAILED DESCRIPTION OF THE INVENTION

The term "sucrose fatty acid lower esters" as used herein refers to mono-, di-, and tri-esters of sucrose and mixtures thereof.

The term "fatty acids" used in the specification and claims means organic fatty acids having at least two and as many as twenty-four carbon atoms, and may be saturated or unsaturated and may have straight or branched chains. Examples of fatty acids that can be used in this invention are myristic, palmitic, stearic, oleic, linoleic and behenic acids. Mixtures of fatty acids may also be used; for example, fatty acids derived from natural triglycerides such as soybean, peanut, coconut, cottonseed, palm, palm kernel, corn, olive, safflower, or sunflower oils.

The total amount of fatty acids present in the reaction mixture can be a maximum that theoretically will react to completely esterify all the free hydroxyls of the sucrose lower esters. In general then, the total amount of fatty acid will be one mole for each mole of free hydroxyl moieties available on the sucrose lower ester reactant. For example, six moles of fatty acid will be present in a reaction with one mole of sucrose diester.

The term "sucrose fatty acid polyesters" as used herein refers to those having an average degree of substitution of 4 to 8.

The term "solvent" used in the description and claims means any material that is liquid at the synthesis reaction temperature and pressure and will dissolve, suspend or hold the fatty acids and sucrose lower esters in the reaction mixture in an amount effective to expedite contact of the reactants for the desired esterification to produce sucrose polyesters. Examples of suitable solvents that can be used in this invention are anhydrous aprotic solvents such as tetrahydrofuran. Other ethers (diethyl ether, dioxane), aromatic hydrocarbons, halogenated hydrocarbons, nitromethane, and pyridine may be used.

In the practice of the present invention, the sucrose fatty acid lower esters and the fatty acids are coupled in the presence of a condensing agent such as dicyclohexylcarbodiimide. Other carbodiimides, e.g., diethylcarbodiimides, N,N'-carbonyl-di(2-methylimidazole), pentamethyleneketene-N-cyclohexylimine, diphenylketene-N-cyclohexylimine, alkoxyacetylenes, 1-alkoxy-1-chloroethylenes, tetraalkyl phosphites, isopropyl polyphosphate, phosphorus oxychloride, phosphorus trichloride, thionyl chloride, oxalyl chloride, and triphenyl phosphines may also be used. Theoretically, one mole of condensing agent reacts with one mole of fatty acid and one mole of free sucrose hydroxyl groups in the coupling reaction. However, best results are achieved by using a slight excess of condensing agent over the theoretical toichiometric amount required. Typically, 1 to 1.2 moles of condensing agent, preferably 1.15, are used.

The esterification reaction is carried out in the presence of a catalyst, including hypernucleophilic agents, such as, for example, 4-dimethylaminopyridine. Other nucleophilic tertiary amines (pyridine, 4-dimethylaminopyridine, 4-morpholino-pyridine, 4-diethylaminopyridine, 4-methoxy-pyridine, and tralkylamines), tetraalkylammonium hydroxide, and inorganic bases (sodium hydrogen carbonate, sodium carbonate, potassium carbonate, and barium carbonate) may also be used. In the reaction mixture, an equimolar proportion of catalyst and sucrose lower ester is used preferentially.

According to a preferred embodiment of the present invention, the sucrose lower fatty acid ester is dissolved in an effective amount of solvent with fatty acids and catalyst. To this solution is added a solution of the condensation agent dissolved in the same solvent. The reaction mixture may be warmed at reflux to speed and stir the reaction. The length of reaction time varies with the reaction conditions and may require several days.

The sucrose polyester end product obtained in the condensation reaction can be separated from contaminants by solvent extraction and washing, as, for example, by concentrating the product in vacuuo, taking it up in ether or other suitable solvent and acid washing followed by drying and filtration, and removing the ether by evaporation. It may be further purified in a known manner, such as by way of chromatography conducted in a usual manner, for example, by using silica gel as adsorbent and hexane as a developer.

The following example details one method for producing sucrose polyester in accordance with the present invention. It is to be understood that this example is merely illustrative and is not to be construed as being limitative. All percentages given are weight percentages, and are based on the weight at the particular stage of processing described.

EXAMPLE

In this example, oleic acid is coupled to sucrose distearate to form predominantly hepta and octaesters.

A 250-mL flask equipped with a reflux condenser and a drying tube is charged with 7.2 grams (0.035 mole) 1,3-dicyclohexylcarbodiimide dissolved in 30 mL tetrahydrofuran. To this is added a solution of 4.6 grams (0.005 mole) sucrose stearate (Ryoto SPE-570, containing an average of two fatty acid residues per molecule sucrose), 0.6 grams (0.005 mole) 4-dimethylaminopyridine, and 8.48 grams (0.03 mole) oleic acid dissolved in 100 mL tetrahydrofuran. The mixture is warmed at reflux for four days and then concentrated in vacuuo. The residue obtained is dissolved in 200 mL diethyl ether, washed with 100 mL 5% HCl, and dried over sodium sulfate. Following filtration, the ether is evaporated and the residue is dissolved in hexane and subjected to flash chromatography on silica gel. Evaporation of the hexane eluant affords a colorless, slightly opaque oil.

Elemental Analysis for $C_{143.4}H_{259.6}O_{18.3}$ formula weight 2276.81: Calculated (%): C: 75.65; H: 11.49; O: 12.86; Found (%): C: 75.47; H: 11.70

NMR Spectrum in $CDCl_3$: chemical shift in ppm (multiplicity, intensity, assignment): 5.34 (multiplet, 11.6 H, HC=CH); 3.88 and 3.68 (broad apparent triplet and multiplet, respectively, 15 H, sucrose CH and OH); 2.39 (triplet, 14 H, $CH_2$-$CO_2$); 2.0, 1.9–1.5, and 1.28 (multiplets, 278 H, $CH_2$); and 0.88 (triplet, 21.8 H, $CH_3$). Analysis of the NMR results supports a composition having a 7.3:1 ratio of fatty acids: sucrose.

The above description is for the purpose of disclosing to a person skilled in the art how to practice the present invention. This description is not intended to detail all the obvious modifications and variations of the invention which will become apparent upon reading. However, applicants do intend to include all such obvious modifications and variations within the scope of their invention which is defined by the following claims.

What is claimed is:

1. A process for synthesizing sucrose fatty acid polyesters comprising reacting a lower sucrose fatty acid ester selected from the group consisting of mono-, di- or tri-esters of fatty acids or mixtures thereof with fatty acids in a solvent in the presence of an effective amount of a carbodiimide.

2. A process according to claim 1 wherein the lower sucrose fatty acid ester is a diester.

3. The process according to claim 2 wherein the diester is sucrose stearate.

4. The process according to claim 1 wherein the fatty acid comprises one or more $C_6$ to $C_{24}$ fatty acids.

5. The process according to claim 1 wherein the fatty acids comprise those derived from natural triglycerides selected from the group consisting of soybean, peanut, coconut, cottonseed, palm, corn, palm kernel, safflower or sunflower oils and mixtures with at least one of these.

6. The process according to claim 1 wherein the fatty acid comprises a member selected from the group consisting of palmitic, stearic, oleic, linoleic, myristic, behenic acids and mixtures thereof.

7. The process according to claim 1 wherein the solvent is an aprotic solvent.

8. The process according to claim 7 wherein the solvent is tetrahydrofuran.

9. The process according to claim 1 wherein the process is carried out in the presence of a catalyst selected from the group consisting of 4-dimethylaminopyridine, 4-morpholinopyridine, 4-diethylaminopyridine, and 4-methoxypyridine.

10. The process according to claim 1 wherein the condensation agent is dicyclohexylcarbodiimide.

11. A process for synthesizing sucrose fatty acid polyesters comprising:
   (a) reacting a lower sucrose fatty acid ester selected from the group consisting of mono-, di- or tri-esters of fatty acids and mixtures thereof with fatty acids in a solvent in the presence of an effective amount of a carbodiimide;
   (b) warming at reflux until the reaction is substantially complete; and
   (c) recovering the sucrose polyester thereby produced.

12. The process according to claim 11 wherein the fatty acids comprise a member selected from the group consisting of palmitic, stearic, oleic, myristic, linoleic and behenic acids and mixtures thereof.

13. The process according to claim 11 wherein the solvent is tetrahydrofuran.

14. The process according to claim 11 wherein the process is carried out in the presence of a catalyst selected from a group consisting of 4-dimethylaminopyridine, 4-morpholinopyridine, 4-diethylaminopyridine, and 4-methoxypyridine.

15. The process according to claim 11 wherein the condensation agent is dicyclohexylcarbodiimide.

16. A method for the condensation of a lower sucrose fatty acid ester with a fatty acid comprising:
   (a) dissolving the lower sucrose fatty acid ester and the fatty acid in an effective amount of solvent;
   (b) adding a carbodiimide dissolved in an effective amount of the solvent;
   (c) reacting the resulting mixture; and
   (d) recovering the sucrose polyester reaction product.

17. A method according to claim 16 wherein the lower sucrose fatty acid ester is a diester.

18. A method according to claim 17 wherein the diester is sucrose stearate.

19. A method according to claim 16 wherein the fatty acid comprises one or more $C_6$ to $C_{24}$ fatty acids.

20. A method according to claim 16 wherein the fatty acid is selected from the group consisting of oleic, palmitic, myristic, stearic, linoleic, behenic and mixtures thereof.

21. A method according to claim 16 wherein the solvent is an aprotic solvent.

22. A method according to claim 21 wherein the solvent is tetrahydrofuran.

23. A method according to claim 16 wherein the carbodiimide is dicyclohexylcarbodiimide.

24. In a process for producing sucrose fatty acid polyester, the improvement which comprises the steps of:
   (a) dissolving 1 mole of a sucrose diester, 4 moles of a fatty acid, and 1 mole of a catalyst in an effective amount of solvent;
   (b) adding 1 to 1.2 moles of a carbodiimide dissolved in an effective amount of the solvent;
   (c) refluxing the mixture until the sucrose esterification is substantially complete; and
   (d) recovering the sucrose fatty acid polyester from the residue.

25. A process according to claim 24 wherein the sucrose diester is sucrose stearate.

26. A process according to claim 24 wherein the fatty acid is oleic acid.

27. A process according to claim 24 wherein the solvent is tetrahydrofuran.

28. A process according to claim 24 wherein the catalyst is 4-dimethylaminopyridine.

29. A process according to claim 24 wherein the carbodiimide is dicyclohexylcarbodiimide.

30. A process for producing sucrose fatty acid polyesters by the dicyclohexylcarbodiimide coupling of a sucrose lower fatty acid ester with fatty acids in the presence of a catalyst in tetrahydrofuran.

31. A process according to claim 30 wherein the catalyst is 4-dimethylaminopyridine.

* * * * *